United States Patent [19]
Miller et al.

[11] Patent Number: 5,395,371
[45] Date of Patent: Mar. 7, 1995

[54] SPINAL FIXATION SYSTEM

[75] Inventors: David F. Miller; Robert A. Farris, both of Memphis, Tenn.; John P. Barrett, Jackson, Miss.

[73] Assignee: Danek Group, Inc., Memphis, Tenn.

[21] Appl. No.: 89,399

[22] Filed: Jul. 8, 1993

Related U.S. Application Data

[63] Continuation of Ser. No. 965,517, Oct. 23, 1992, abandoned, which is a continuation of Ser. No. 730,115, Jul. 15, 1991, abandoned.

[51] Int. Cl.$^6$ ............................................. A61F 5/04
[52] U.S. Cl. ...................................... 606/61; 606/72; 606/73
[58] Field of Search ..................... 606/60, 61, 72, 73

[56]  References Cited

U.S. PATENT DOCUMENTS

| | | | |
|---|---|---|---|
| 4,611,681 | 9/1986 | Steffee | 128/69 |
| 4,696,290 | 9/1987 | Steffee | 128/69 |
| 4,790,297 | 12/1988 | Luque | 128/69 |
| 4,836,196 | 6/1989 | Park et al. | 128/69 |
| 4,887,595 | 12/1989 | Heinig et al. | 128/69 |
| 5,084,048 | 1/1992 | Jacob et al. | 606/61 |
| 5,092,867 | 3/1992 | Harms et al. | 606/61 |
| 5,129,899 | 7/1992 | Small et al. | |

OTHER PUBLICATIONS

Matsuzaki et al., "Problems and Solutions of Pedicle Screw Plate Fixation of Lumbar Spine," *Spine*, vol. 15, No. 11, 1990, pp. 1159–1165.

*Primary Examiner*—Richard J. Apley
*Assistant Examiner*—Linda C. M. Dvorak
*Attorney, Agent, or Firm*—Woodard, Emhardt, Naughton, Moriarty & McNett

[57]  ABSTRACT

A a spinal fixation system comprises an elongated fixation plate having a bottom side for facing the vertebrae, an opposite top side extending generally parallel to the bottom side, and an elongated slot defined therethrough which extends substantially along the length of the plate. The slot has a lower edge at the intersection of the slot and the bottom surface and an upper edge at the intersection of the slot and the top surface with a number of concave depressions formed at each edge. In one embodiment, the concave depressions at the lower and upper edges of the slot form comparable scalloped surfaces. In another embodiment, the lower edge of the slot forms a single concave surface extending around the entire perimeter of the lower edge of the slot. The system further includes a pedicle screw and a nut for load transmission between the vertebrae and the fixation plate. The pedicle screw includes a threaded nut engaging portion, a threaded bone engaging portion and an intermediate portion therebetween. The intermediate portion has a rigid upper arcuate surface facing toward the nut engaging portion which is substantially complementary to the concave depressions in lower edge of the slot. The nut includes a threaded head portion for engaging the nut engagement portion of the pedicle screw, and a rigid lower arcuate surface which is substantially complementary to the concave depressions at the upper edge of the slot. In the assembled configuration of the spinal fixation system, the fixation plate is supported by the upper arcuate surface of the pedicle screw and is clamped between the pedicle screw and the nut. The concave depressions and the upper and lower arcuate surfaces coact to permit angulation of the pedicle screw relative to the elongated plate while maintaining load transmitting contact over a wide range of angles of the pedicle screw relative to the fixation plate.

7 Claims, 3 Drawing Sheets

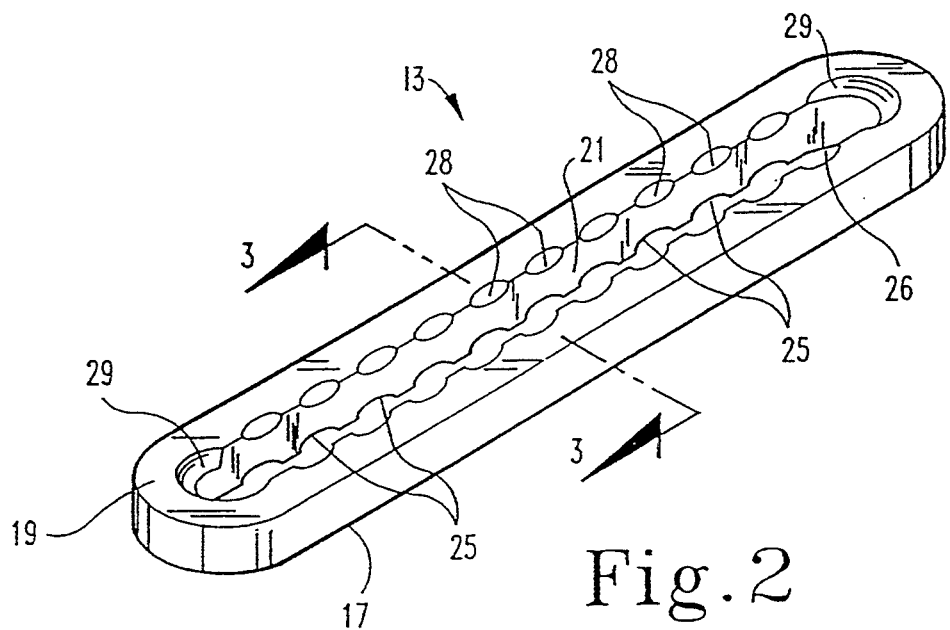
Fig. 2
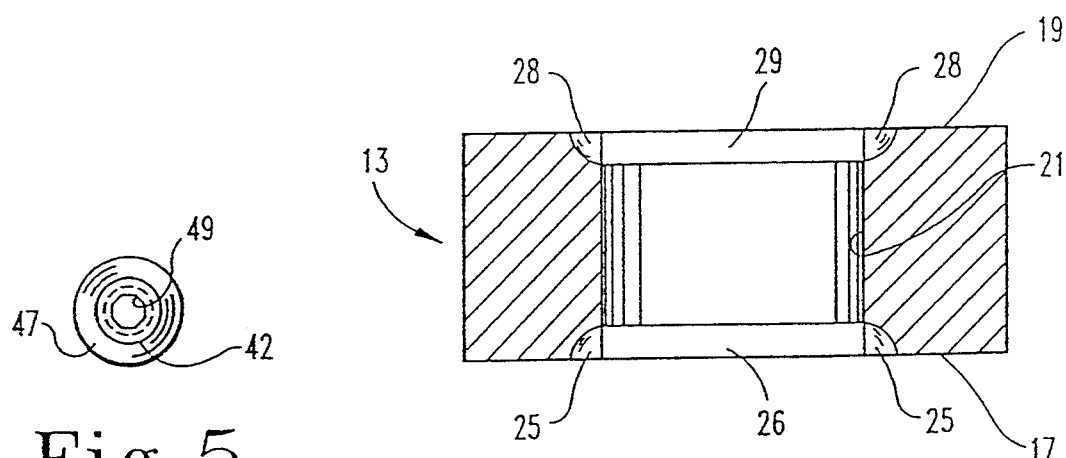
Fig. 5
Fig. 3
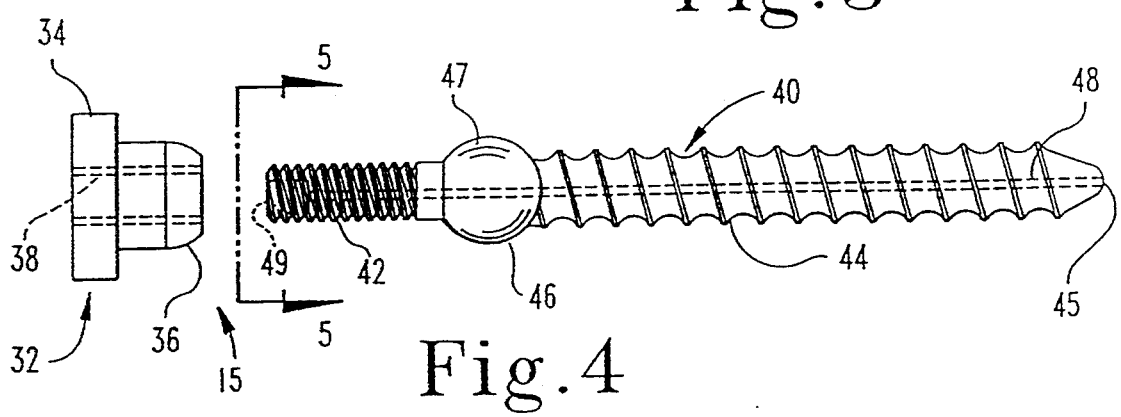
Fig. 4

SPINAL FIXATION SYSTEM

This application is a continuation of application Ser. No. 07/965,517, filed Oct. 23, 1992, now abandoned, which is a continuation of application Ser. No. 07/730,115, filed Jul. 15, 1991, also now abandoned.

BACKGROUND OF THE INVENTION

The present invention relates to spinal fixation methods and systems. In particular, the invention concerns a fixation plate and bone screw system for attachment to vertebral bodies to hold the vertebrae in alignment.

Within the last few decades, spinal fixation systems have been developed using generally rigid plates which are engaged between vertebrae of the spine, typically on opposite sides of the spinous processes. One such type of spinal plate is illustrated in the patents to Steffee, U.S. Pat. Nos. 4,611,581 and 4,696,290. In this device, a spinal plate is provided which has a series of openings therein for receiving the threaded portions of force transmitting members. The force transmitting members comprise a dual-threaded screw which includes a first threaded portion for engaging the bone of the vertebrae, and a second threaded portion which projects outwardly from the vertebrae and through the openings in the spinal plate. The dual-threaded bone screws in the Steffee apparatus are engaged to the bone plate by way of a nut which is tightened onto the second threaded portion of the force transmitting members and against the plate. The spinal plate described in the Steffee references includes a number of bridge elements between the elongated openings in the plate which tend to increase the rigidity of the plate.

Another type of spinal fixation system is shown in the patent to Luque, U.S. Pat. No. 4,790,297, which has been assigned to the assignee of the present invention. In this system, a spinal fixation plate includes a single elongated opening which extends substantially across the length of the plate. A number of depressions are formed in the top surface of the plate at the edge of the central elongated opening. These depressions are used to engage a convex portion of a bone screw which extends through the opening in the bone plate and into the vertebral bone. The system also includes a plate ring which encircles the plate to prevent the plate from spreading when the bone screws are tightened down onto the bone plate. The plate ring can be situated at any position along the length of the fixation plate.

One difficulty encountered by prior plating fixation systems is the failure of the pedicle screw. For instance, with the Steffee system, the first threaded portion (or bone screw portion) includes a nut surface which contacts the bottom face of the fixation plate when the separate nut is tightened against the top face of the plate. In practice it has been found that the nut surface does not contact flush against the bottom face of the fixation plate, thereby leaving an unsupported section of the second threaded or nut engagement portion exposed beneath the plate. This results in stress risers in the second threaded portion which are susceptible to fatigue failure under the cyclic loads generated by spinal motion. An increase in the angular deviation or angulation of the screw to the fixation plate in the Steffee system may increase the stresses and the likelihood of fatigue failure.

Another related disadvantage of some of the prior spinal fixation systems using a generally rigid bone plate is that the plates do not permit a beneficial amount of angulation between the bone screws and the plate, which may be required to account for various angles of fixation to the vertebrae or to accommodate normal sagittal curvature of the spine. In these prior devices, this angulation is often provided by bending the bone plate itself to conform to curvature between adjacent vertebrae. Bending the plate presents difficulty in properly aligning the pedicle screw with the vertebrae.

Optimally, in plate spinal fixation systems, a compromise in stiffness and rigidity of the system is required so that the system is stiff enough to challenge the bone to facilitate bone fusion of the spine, and not so rigid that normal loads on the spine will lead to fatigue failures of the bone screws. Present fixation systems do not appear capable of achieving this compromise.

There is therefore a need for a spinal fixation system which can more easily compromise the rigidity needs for bone growth and for protection of the fixation system components. In other words, the need exists for a fixation system that has increased stiffness characteristics without the accompanying tendency for fatigue failures.

There is also a need for a spinal fixation system that is capable of achieving angulation between the bone-engaging screws without the necessity of bending and forming the bone plate itself. A further need exists for a spinal fixation system in which the load transmitted from the vertebral bone to the force transmitting member can be transmitted to the fixation plate at an angle other than generally perpendicular to the plate surface.

BRIEF DESCRIPTION OF THE DRAWINGS

FIG. 2 is a perspective view of the fixation plate means of the spinal fixation system of the present invention.

FIG. 3 is a cross-sectional view of the fixation plate means in FIG. 2 taken along line 3—3 as viewed in the direction of the arrows.

FIG. 4 is an exploded side elevation view of the load transmitting means of the spinal fixation system of the present invention.

FIG. 5 is an end view of the pedicle screw means of the load transmitting means shown in FIG. 4 taken along line 5—5 as viewed in the direction of the arrows.

SUMMARY OF THE INVENTION

Figure 1:
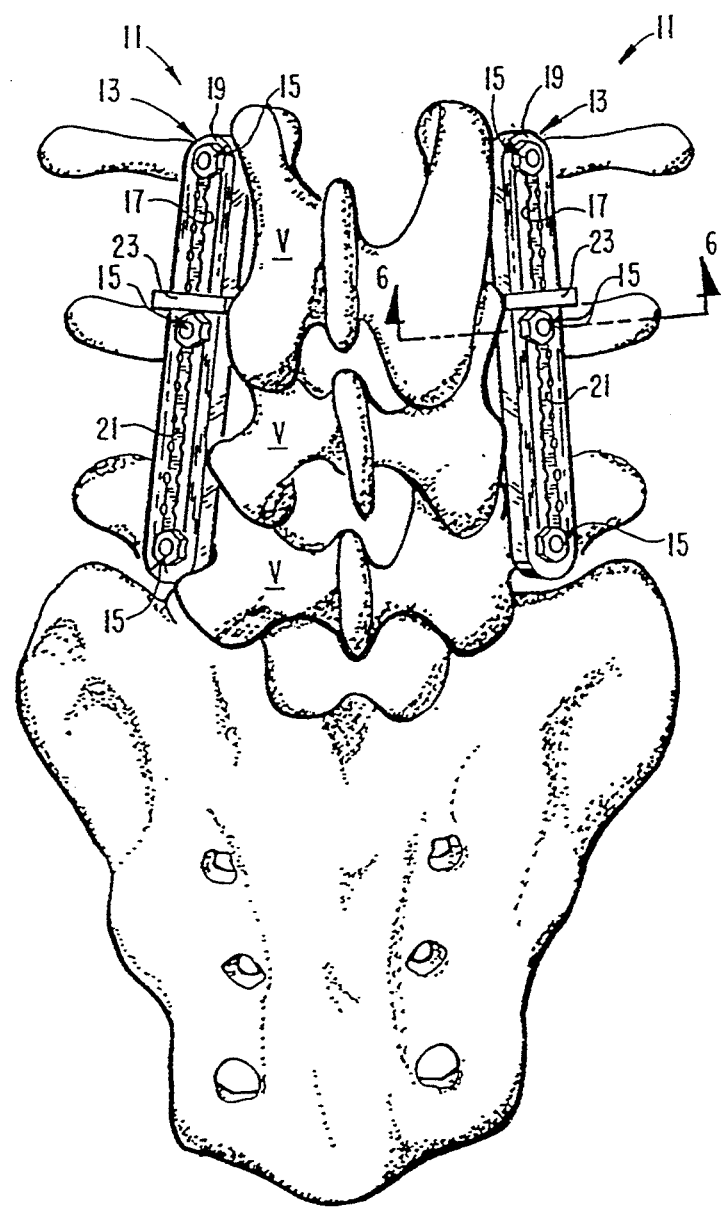
FIG. 1 is a pictorial plan view of a portion of a patient's spinal column with a pair of the spinal fixation systems according to the present invention secured thereto.

The present invention provides a spinal fixation system which addresses the problems encountered by prior such systems. According to one embodiment of the invention, the system comprises an elongated plate having a bottom side for facing the vertebrae and an opposite top side extending generally parallel to the bottom side. The plate further includes an elongated slot defined therethrough between the bottom side and the top side which extends substantially along the length of the plate. The slot has a lower edge at the intersection of the slot and the bottom surface and an upper edge at the intersection of the slot and the top surface. A number of first concave depressions are formed at the lower edge of the slot and a number of second concave depressions are formed at the upper edge of the slot. In one embodiment, the concave depressions at the upper edge of the slot form a scalloped surface. The lower edge depressions may also form a comparable scalloped surface corresponding to the upper scallops. In another embodiment, the number of first concave depressions at the slot lower edge is a single concave surface extending around the entire perimeter of the lower edge of the slot.

The system further comprises load transmitting means for engagement between the vertebrae and the elongated plate for transmitting forces therebetween. This load transmitting means includes pedicle screw means having a first threaded portion, a second threaded portion and an intermediate portion between with the first and the second threaded portions. The second threaded portion includes a number of threads adapted to engage the bone of the vertebrae. The intermediate portion has a rigid upper arcuate surface facing toward the first threaded portion, which upper arcuate surface is substantially complementary to the number of first concave depressions in the fixation plate to be received therein. The load transmitting means also includes a nut having a threaded head portion for engaging the first threaded portion of the pedicle screw means and a rigid lower arcuate surface. The lower arcuate surface is substantially complementary to the number of second concave depressions at the upper edge of the slot to be received therein.

In the assembled configuration of the spinal fixation system, the pedicle screw means is threaded into the vertebra with the first threaded portion extending outward. The fixation plate is supported by the intermediate portion of the pedicle screw means, and particularly against the upper arcuate surface. The nut is tightened down along the first threaded portion until it clamps the fixation plate between the intermediate portion of the pedicle screw means and the nut. The lower arcuate surface of the nut is received within an upper concave depression while the upper arcuate surface of the pedicle screw means is received within a lower concave depression.

In one aspect of the invention, the first and second concave depressions and the upper and lower arcuate surfaces coact to permit angulation of the pedicle screw means relative to the elongated plate. The arcuate surfaces and concave depressions maintain in load transmitting contact over a wide range of angles so that forces generated by motion of the spinal column are efficiently transmitted to the fixation plate even when the pedicle screw means are at an angle to the plate.

It is one object of the plate spinal fixation system of the present invention to achieve an optimum compromise in stiffness and rigidity of the system so that the system is stiff enough to challenge the bone to facilitate bone fusion of the spine, and not so rigid that normal loads on the spine will lead to fatigue failures of the bone screws. Another object is to provide a spinal fixation system that is capable of achieving angulation between the bone-engaging screws without the necessity of bending and forming the bone plate itself.

A further object resides in a spinal fixation system in which the load transmitted from the vertebral bone to the load transmitting member can be efficiently transmitted to the fixation plate at an angle other than generally perpendicular to the plate surface. A related object is to permit load transmission at angles to the fixation plate without creating stress risers or concentrations in the force transmitting member. Other objects, as well as certain benefits, of the present invention will become apparent from the following written description and accompanying figures.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In a preferred embodiment of the invention, a spinal fixation system 11 is depicted in FIG. 1 which is sued for segmental fixation of the vertebrae V of a spinal column. The spinal fixation system 11 comprises, in general, a substantially rigid spinal plate means or plate 13 and at least a pair of load transmitting means 15. Typically, a fixation system 11 is utilized on each side of the spinal column or spinous processes, as shown in FIG. 1, and may be used to fix a plurality of levels of the spinal column, as will be apparent to those skilled in the art. The load transmitting means 15 are engaged with the vertebrae and operate to transmit forces from the spinal column to the fixation plate means 13.

Figure 6:
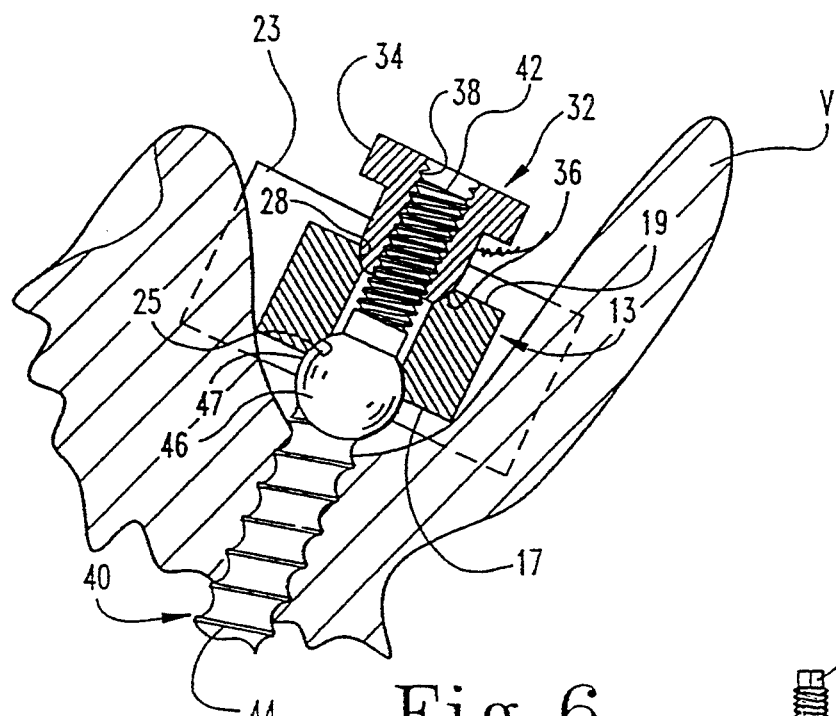
FIG. 6 is an enlarged sectional view of a vertebrae with the spinal fixation system attached thereto, taken along 6—6 in FIG. 1 as viewed in the direction of the arrows.

Plate ring means or plate ring 23 is provided with the spinal fixation system 11 which at least substantially encircles the fixation plate means 13 (see also FIG. 6). The construction and object of the plate ring 23 of the present invention is substantially as shown and described in the commonly owned patent to Luque, U.S. Pat. No. 4,790,297. (For instance, see column 4, lines 1-12 of the subject patent.) For purposes of the present invention, the plate ring 23 encircles the fixation plate 13 to prevent the plate 13 from spreading when the load transmitting means 15 are tightened or snugged down onto the plate 13. The plate ring 23 can comprise a substantially rectangular body having a substantially rectangular slot therethrough for allowing the plate ring 23 to slide over the plate 13.

Referring to FIGS. 2 and 3, the fixation plate means or plate 13 is illustrated as having a first or bottom side 17 and an opposite second or top side 19. The bottom side 17 is directed toward the vertebrae V when the spinal fixation system 11 is in its operative position, while the top side 19 is directed away from the vertebrae. The plate 13 has an elongated slot 21 extending between the bottom and top sides 17 and 19 substantially along the longitudinal length or axis of the plate 13. The lower edge of the slot 21 adjacent the bottom side 17 of the plate includes a plurality of lower concave depressions 25. Similarly, the upper edge of the slot 21 adjacent the top side 19 of the plate includes a comparable plurality of upper concave depressions 28. At the bottom side of the plate 17, a pair of opposite lower end depressions 26 are formed at the end of slot 21. A comparable pair of upper end depressions 29 are situated at the ends of the elongated slot 21 at the top side 19 of the plate 13.

Concave depressions 25 and 28 are preferably positioned completely around all sides of the slot 21 at the bottom and top sides of the plate in a spaced side-by-side relationship. The concave depressions 25 or 28 at either side 17 or 19 of the plate are aligned on opposite sides of the slot 21. Moreover, the depressions 25 on the bottom side 17 are aligned with the depressions 28 on the bottom side 19. The plate 13 thus appears as a "double-scalloped" plate, with a scalloped upper surface and a scalloped lower surface.

The plate 13 may be constructed in various manners. For instance, the slot and depressions may be machined out of a stainless steel bar of various lengths from 1 to 4 inches. The depressions 25, 26, 28 and 29 are preferably formed by spherical cuts in the bar, having, in one specific embodiment, a diameter of 0.315 inches.

The load transmitting means 15, shown in detail in FIG. 4, includes a spherical nut 32 and pedicle screw means 40. The nut 32 includes a head portion 34, which is preferably configured as a hex head for engagement by a tightening tool, such as a wrench. The nut 32 further includes a lower arcuate surface 36 which is disposed within the upper concave depressions 28 or upper end depressions 29 at the top side 19 of the plate 13 when the fixation system is in its operative position. Thus, the diameter of the lower arcuate surface 36 is preferably equal to the diameter of the upper depressions 28 and 29. The spherical nut 32 includes internal female threads for engaging the pedicle screw means 40 of the load transmitting means 15.

The pedicle screw means 40 includes an elongated shaft having a first threaded portion 42 and a second threaded portion 44. The first threaded portion 42 includes a number of male threads which are adapted to engage the internal threads 38 of the spherical nut 32. The second threaded portion 44 is configured into a bone helix with a substantially blunt end 45. The threads of the bone helix are adapted to engage the bone tissue of the vertebrae V into which the pedicle screw means 40 is threaded. The configuration of the bone helix of the second threaded portion 44 can be constructed in various manners and in various sizes known to those skilled in the art.

The shaft of the pedicle screw means 40 also includes an integral intermediate portion 46 between the first threaded portion 42 and the second threaded portion 44, so that the pedicle screw means 40 defines a dual-threaded bone screw. In one embodiment, the intermediate portion includes an upper arcuate surface 47. The upper arcuate surface 47 is adapted to engage the lower concave depressions 25 and 26 in the bottom side 17 of the plate 13. The diameter of the upper arcuate surface 47 is preferably spherical in configuration and has a diameter at least equal to the diameter of the lower concave depressions 25 and 26. In the illustrated embodiment, the intermediate portion 46 is shown as substantially spherical. However, it is understood that the intermediate portion 46 may be truncated leaving only the upper arcuate surface 47.

The pedicle screw means 40 is provided with a cavity 49 formed in the end of the pedicle screw means adjacent the first threaded portion 42. Preferably, the cavity 49 is hexagonal in configuration for engaging an insertion tool. The pedicle screw means 40 may also be cannulated to include a bore 48 extending through the entire length of the screw means.

To insert the pedicle screw means 40 into the vertebrae, the preferred spinal fixation method calls for tapping the vertebrae V using a screw tap as is known in the art. Tapped threads can be made in each of the levels of the spinal column to which the spinal fixation system 11 is to be fixed. For instance, as shown in FIG. 1, threads are tapped into three vertebrae V. The pedicle screw means 40 can then be threaded into the tapped bone opening by using a suitable driving too engaged within the hex cavity 49 at the end of the pedicle screw means 40. A guide wire temporarily inserted into the bone can be used to properly align the pedicle screw means as it is threaded into the bone opening, in which instance the guide wire extends through the bore 48.

The pedicle screw means 40 is preferably threaded into the bone to a predetermined depth that is ascertained so that the upper arcuate surface 47 can contact the lower concave depressions 25 of the fixation plate means while the fixation plate 13 is situated between processes of the vertebrae V, as shown FIG. 6. Thus, as shown in FIG. 6, the intermediate portion 46 of the pedicle screw means 40 does not contact the vertebra.

Once a pedicle screw means 40 has been threaded into each of the tapped openings in the vertebrae V, the fixation plate 13 can be placed against the arcuate surfaces 47 of each of the pedicle screw means 40. It is understood that the lower concave depressions 25 and the upper arcuate surfaces 47 of each of the pedicle screw means 40 coact to permit angulation between the pedicle screw means and the fixation plate means. In other words, the pedicle screw means is permitted to fit the plate 13 at several angles to accommodate abnormal pedicle conditions. Once, the fixation plate has been properly aligned and situated with concave depressions 25 contacting the upper arcuate surfaces 47 of pedicle screw means 40, a spherical nut 32 can be engaged onto the first threaded portion 42 of each of the pedicle screw means.

The spherical nut 32 is then tightened down along the first threaded portion 42 until the lower arcuate surface 36 of the nut 32 engages the upper concave depressions 28 of the fixation plate 13. Again, the lower spherical surface 36 of the nut 32 and the upper concave depressions 28 coact to allow the pedicle screw means 40 to fit the plate 13 at various angles. Moreover, the lower spherical surface 36 and upper concave depressions 28 provide means for aligning the pedicle screw means 40 along the length of the fixation plate 13. The coaction of these two surfaces prevents the pedicle screw means from migrating along the length of the plate under loading from the spinal column.

Figure 7:
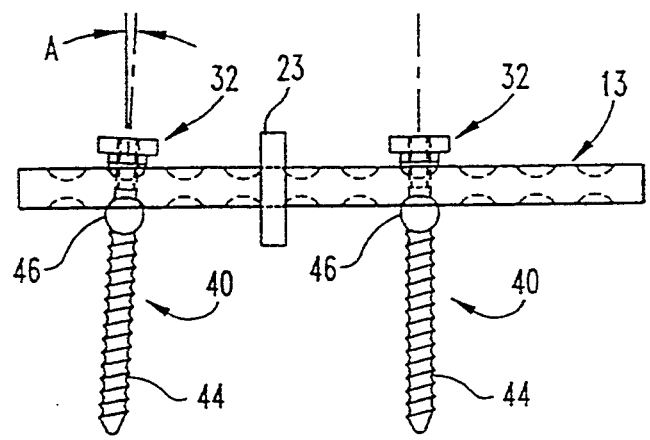
FIG. 7 is a side schematic representation of the spinal fixation system of the present invention showing a pair of load transmitting means at different relative angles to each other.

As shown in FIG. 7, a pair of pedicle screw means 40 can be engaged within vertebrae, not shown in the figure, at differing angles. The leftmost pedicle screw means 40 is shown situated at an angle "A" relative to a perpendicular to the plate 13, while the right-most pedicle screw means 40 is oriented perpendicular to the plate. Unlike prior spinal fixation systems, the present embodiment of the invention provides spherical contacts at the top and bottom sides of the fixation plate between the fixation plate 13 and the load transmitting means 15. These spherical contacts permit angulation between the components when the spinal fixation system is installed in a patient. Moreover, the spherical contacts allow the load from the spinal column passing through the vertebrae V to the load transmitting means 15 to be more efficiently transmitted to the fixation plate 13 even when the pedicle screw means is at an angle "A" as depicted in FIG. 7.

The combination of the fixation plate means 13 and the load transmitting means 15 of the present invention provides a beneficial compromise between the need to control the loads exerted upon the pedicle screw means 40 and the need to challenge the bone tissue to facilitate bone fusion. As a further advantage, the single slot 21 of the plate means 13 within which the load transmitting means 15 react allows a spring action in the plate as the plate 13 spreads under increasing loads. The coaction between the arcuate surfaces of the fixation plate and the load transmitting means particularly provides for spring action when the pedicle screw means is at an angle relative to the fixation plate, as illustrated in FIG. 7. This spring action enhances the fatigue life of the load transmitting means. The addition of the plate ring means 23 to the spinal fixation system 11 controls the amount of spreading of the fixation plate 13 as the spinal fixation system is loaded and unloaded to maintain an optimum load on the vertebrae V. The arcuate scallops or depressions 25 and 28 also act as a buttress against increases in angulation of the pedicle screw means 40, thereby tending to keep the pedicle screw means in its initial angular orientation.

Figure 8:
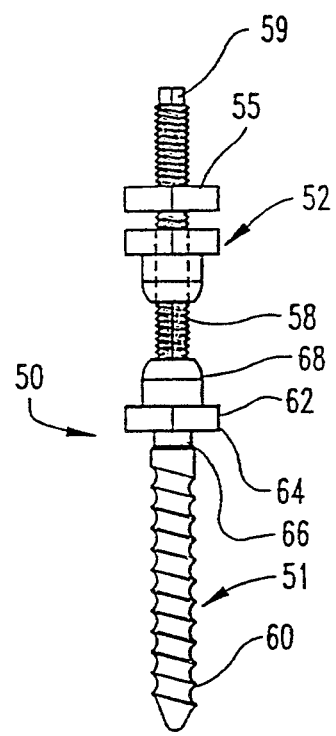
FIG. 8 is a side elevational representation of the load transmitting means of an alternative embodiment of the spinal fixation system of the present invention.
Figure 9:
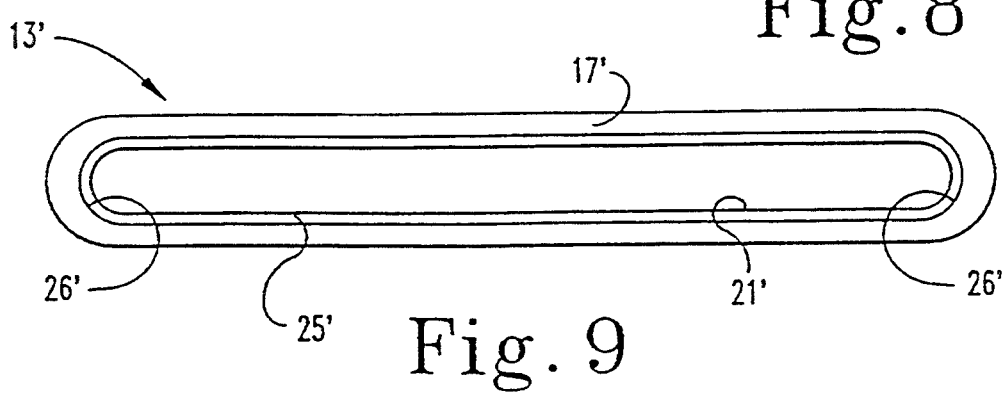
FIG. 9 is a bottom elevation view of an alternative embodiment of a fixation plate means for use with the spinal fixation system of the present invention.

Referring to FIG. 8, an alternative embodiment of the load transmitting means, depicted as means 50, includes a pedicle screw means 51 and a spherical nut means 52. The load transmitting means 50 further includes a locknut 55 which can be threaded on the pedicle screw means against the nut means 52 to maintain the position of the nut means relative to the pedicle screw means 51. The pedicle screw means 51 includes a second threaded portion 60 which is substantially similar to the bone screw portion 44 of the previous embodiment. In a variation from the previous embodiment of the pedicle screw means 40, the screw means 51 includes a longer first threaded portion 58 which extends substantially away from the surface of the fixation plate 13. The end 59 of the first threaded portion 58 can be formed to engage a driving or insertion tool. The locknut 55 and spherical nut means 52 are threaded onto the extended first threaded portion 58 against the fixation plate 13. It is understood that the excess length of the first threaded portion 58 can be severed just above the locknut 55.

The pedicle screw means 51 includes an intermediate portion 62. This intermediate portion includes a driving portion 64 which is connected to the second threaded or bone screw portion 60 by a necked down segment 66. An arcuate surface 68 is formed at the top face of the driving portion 64 adjacent and integral with the first threaded portion 58. This arcuate surface 68 is substantially identical to the arcuate surface 47 of the pedicle screw means 40 of the previous embodiment. It can be noted that while the arcuate surface 68 of this embodiment is integral with the first and second threaded portions, an additional spherical nut like the nut means 52 can be inverted and threaded onto the first threaded portion to provide the arcuate surface. In this modification, the spherical surface 68 would be eliminated in favor of the inverted spherical nut which would be threaded down onto the driving portion 64 of the integral intermediate portion 62.

In an alternative embodiment of the fixation plate means of the present invention, a fixation plate means or plate 13' is provided which is substantially similar to the fixation plate 13 shown in FIGS. 2 and 3. However, with this alternative embodiment, the elongated slot 21' includes a single concave surface 25' which extends along substantially the entire perimeter of the slot 21', at the first or bottom side 17' of the plate 13'. The lower concave surface 25' terminates in lower end depressions 26' at opposite ends of the elongated slot 21'.

The opposite or top side of the plates preferably includes a plurality of upper concave depressions (not shown), such as the depressions 28 and 29 of the previous embodiment of plate 13. Thus concave depressions in the top side of the plate provide means for locating a load transmitting means, such as means 15 or 50, along the longitudinal length of the fixation plate 13'. The lower concave surface 25' at the bottom side 17' of the plate 13' allows for even greater angularity of the load transmitting means relative to the fixation plate 13' than normally permitted by the previous double-scalloped plate 13.

In this embodiment, as in the previous embodiment of the fixation plate, the arcuate surfaces of the load transmitting means remain in contact with the concave surfaces at the top and bottom of the plate 13', even at relative large angles, to efficiently transmit forces from the spine to the fixation plate. However, while this embodiment permits greater angulation, the spring or buttressing effect is reduced from the double-scalloped version of the previous embodiment since the pedicle screw means may slide somewhat along the lower concave surface 25' under certain loads.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For instance, each of the components of the spinal fixation system of the present invention may be machined from stainless steel stock. It is understood that other suitable materials may be identified by those of ordinary skill in the art.

In addition, while spherical surfaces for the pedicle screw means and fixation plates have been depicted and described, other arcuate surfaces are contemplated by this invention. Likewise, other surface configurations are contemplated that permit angulation between the fixation plate and the pedicle screw means.

What is claimed is:

1. A spinal fixation system for maintaining vertebrae in a desired relationship comprising:
    an elongated plate having;
        a bottom side for facing the vertebrae;
        an opposite top side extending generally parallel to said bottom side;
        an elongated slot defined therethrough between said bottom side and said top side and extending substantially along the length of said plate, said slot having a lower edge at the intersection of said slot and said bottom surface and an upper edge at the intersection of said slot and said top surface, and
        a number of first concave depressions formed at said lower edge of said slot and a number of second concave depressions formed at said upper edge of said slot; and load transmitting means for engagement between the vertebrae and said elongated plate for transmitting forces therebetween, said load transmitting means including;

a bone screw having an elongated shaft defining a first threaded portion, a second threaded portion and an intermediate portion between said first and said second threaded portions, said second threaded portion including a number of threads adapted to engage the bone of the vertebrae, said intermediate portion having an integral rigid upper arcuate surface facing toward said first threaded portion, said upper arcuate surface being substantially complementary to said number of first concave depressions to be received therein, so that said plate is supported on said arcuate surface; and a nut having a threaded head portion for engaging said first threaded portion and a rigid lower arcuate surface which is substantially complementary to said number of second concave depressions to be received therein when said nut is tightened down along said first threaded portion;

wherein said first and second concave depressions and said upper and lower arcuate surfaces are configured to permit angulation of said bone screw relative to said elongated plate when said second threaded portion is engaging the bone of the vertebrae while said upper arcuate surface is in contact with said number of first concave depressions and said lower arcuate surface is in contact with said number of second concave depressions.

2. The spinal fixation system of the claim 1, wherein said elongated slot includes:
   a plurality of opposite pairs of first concave depressions at said lower edge of said slot; and
   a plurality of opposite pairs of second concave depressions at said upper edge of said slot.

3. The spinal fixation system of the claim 1, wherein said elongated slot includes:
   a lower concave surface formed around substantially the entire perimeter of said lower edge of said slot; and
   a plurality of opposite pairs of second concave depressions at said upper edge of said slot.

4. The spinal fixation system of claim 1, wherein at least said number of first concave depressions of said elongated slot and said upper arcuate surface of said intermediate portion of said bone screw are spherical and define spherical surfaces having substantially the same diameter.

5. The spinal fixation system of the claim 1, wherein at least said number of second concave depressions of said elongated slot and said lower arcuate surface of said nut of said load transmitting means are spherical and define spherical surfaces having substantially the same diameter.

6. The spinal fixation system of claim 1, wherein said bone screw is cannulated.

7. The spinal fixation system of claim 4, wherein said intermediate portion defines a spherical surface opposite said upper arcuate surface facing toward the bone of the vertebra when said second threaded portion is engaging the bone.

* * * * *

UNITED STATES PATENT AND TRADEMARK OFFICE
CERTIFICATE OF CORRECTION

PATENT NO.  : 5,395,371
DATED       : March 7, 1995
INVENTOR(S) : David F. Miller et al.

It is certified that error appears in the above-identified patent and that said Letters Patent is hereby corrected as shown below:

Column 4, line 30, please change "sued" to "used".

Signed and Sealed this

Seventh Day of November, 1995

Attest:

BRUCE LEHMAN

Attesting Officer

Commissioner of Patents and Trademarks